(12) United States Patent
Ganzitti (10) Patent No.: US 11,357,923 B2
(45) Date of Patent: Jun. 14, 2022

(54) ZERO POSITION SENSING SYSTEM FOR MEDICATION DELIVERY DEVICE

(71) Applicant: Eli Lilly and Company, Indianapolis, IN (US)

(72) Inventor: Gabriele Ganzitti, Milan (IT)

(73) Assignee: Eli Lilly and Company, Indianapolis, IN (US)

( * ) Notice: Subject to any disclaimer, the term of this patent is extended or adjusted under 35 U.S.C. 154(b) by 809 days.

(21) Appl. No.: 15/760,835

(22) PCT Filed: Oct. 6, 2016

(86) PCT No.: PCT/US2016/055642
§ 371 (c)(1),
(2) Date: Mar. 16, 2018

(87) PCT Pub. No.: WO2017/066067
PCT Pub. Date: Apr. 20, 2017

(65) Prior Publication Data
US 2018/0250473 A1    Sep. 6, 2018

Related U.S. Application Data

(60) Provisional application No. 62/240,717, filed on Oct. 13, 2015.

(51) Int. Cl.
*A61M 5/315* (2006.01)
*A61M 5/31* (2006.01)

(52) U.S. Cl.
CPC ...... *A61M 5/3157* (2013.01); *A61M 5/31551* (2013.01); *A61M 5/31585* (2013.01);
(Continued)

(58) Field of Classification Search
CPC ................ A61M 5/3157; A61M 5/178; A61M 5/31551; A61M 5/31585;
(Continued)

(56) References Cited

U.S. PATENT DOCUMENTS

| | | |
|---|---|---|
| 8,128,604 B2 | 3/2012 | Yeandel et al. |
| 2004/0210199 A1 | 10/2004 | Atterbury et al. |

(Continued)

FOREIGN PATENT DOCUMENTS

| | | |
|---|---|---|
| WO | 2010052275 | 5/2010 |
| WO | 2014020010 | 2/2014 |

(Continued)

*Primary Examiner* — Brandy S Lee
(74) *Attorney, Agent, or Firm* — M. Daniel Spillman (57) ABSTRACT

A sensing system for determining a zero position of a medication delivery device. The sensing system includes at least one actuator member, a biasing member, a stop surface and a sensor. The stop surface is structured and arranged within the device housing for abutment by a push surface of the at least one actuator member as a screw element of the device screws to a zero position from a dosing position. The abutment forces the at least one actuator member to move relative to the screw element from a first position to a second position against a resistance provided by the biasing member. A sensor within an electronics module is adapted to recognize the at least one actuator member at the second position.

20 Claims, 10 Drawing Sheets

(52) U.S. Cl.
CPC ............ *A61M 2005/3126* (2013.01); *A61M 2205/3306* (2013.01); *A61M 2205/3317* (2013.01); *A61M 2205/3327* (2013.01); *A61M 2205/3375* (2013.01); *A61M 2205/3553* (2013.01); *A61M 2205/50* (2013.01); *A61M 2205/502* (2013.01)

(58) Field of Classification Search
CPC .. A61M 2005/3126; A61M 2205/3306; A61M 2205/3317; A61M 2205/3327; A61M 2205/3375; A61M 2205/3553; A61M 2205/50; A61M 2205/502
See application file for complete search history.

(56) References Cited

U.S. PATENT DOCUMENTS

| | | | |
|---|---|---|---|
| 2014/0074041 A1* | 3/2014 | Pedersen | A61M 5/31541 604/211 |
| 2016/0287804 A1* | 10/2016 | Madsen | G01D 5/1655 |
| 2017/0007765 A1* | 1/2017 | Cowe | A61M 5/172 |

FOREIGN PATENT DOCUMENTS

| | | |
|---|---|---|
| WO | 2015075134 | 5/2015 |
| WO | 2015124923 | 8/2015 |

* cited by examiner

ZERO POSITION SENSING SYSTEM FOR MEDICATION DELIVERY DEVICE

BACKGROUND OF THE INVENTION

The present invention pertains to delivery devices, and, in particular, to a sensing system for determining the zero position of a drive mechanism of a medication delivery device.

A variety of known types of devices are used to deliver fluid medication to a patient. These types of devices include, but are not limited to, injection pens. Some injection pens include electronics to monitor aspects of the pen in order to supply a user with potentially useful information, such as an amount and time of an injection taken most recently as well as other past injections.

When the electronics of an injection pen are used to track an injected dose, it typically detects when that injection is completed. This detection may coincide with the event of the dose setting dial or the like returning back to its initial position that is conventionally called the "zero position". One way to sense a "zero position" is to design the injection pen with two parts that come in contact only during the transition of the device between a position 1 and a position 0, and to detect this contact and transform it into an electrical signal for the device electronics. However, it can be the case that the most available contact point is relatively far removed from the electronics, such as if the electronics are positioned within or near an actuator button that is at the proximal end of the dial and the contact point involves the distal end of the dial, and an electrical lead extends from the electronics to the contact point.

Thus, it would be desirable to provide a system for sensing the zero position that can overcome one or more of these and other shortcomings of the prior art.

BRIEF SUMMARY

In one form thereof, the present invention provides a sensing system for determining a zero position of a medication delivery device. The medication delivery device includes a housing, a screw element, and an electronics module. The screw element is screwable within the housing from a dosing position to a zero position during dose delivery. The sensing system includes at least one actuator member mounted to be movable relative to the screw element from a first position to a second position, the at least one actuator member including a push surface; a biasing member arranged to resist motion of the at least one actuator member from the first position to the second position; a stop surface structured and arranged within the housing for abutment by the push surface as the screw element screws to the zero position from the dosing position, the abutment forcing the at least one actuator member to move from the first position to the second position against resistance provided by the biasing member; and a sensor within the electronics module adapted to recognize the at least one actuator member at the second position.

In another form thereof, the present invention provides a method of sensing a zero position of a medication delivery device having a screw element, a housing, and an electronics module, including the steps of: screwing the screw element within the housing from a dosing position to a zero position during dose delivery; during the step of screwing the screw element from the dosing position to the zero position, abutting at least one actuator member against a stop surface within the medication delivery device housing to cause the at least one actuator member to move around the screwing screw element from a first angular position to a second angular position against resistance provided by a biasing member; and, sensing with a sensor of the electronics module when the at least one actuator member reaches the second angular position.

One advantage of the present invention is that a system for sensing a zero position of a medication delivery device may be provided which does not require an electrical connector extending a significant distance within the device in which such is installed.

Another advantage of the present invention is that a system for sensing a zero position of a medication delivery device may be provided which transfers a motion due to contact at a contact point to the electronics that are spaced from that contact point.

BRIEF DESCRIPTION OF THE DRAWINGS

The above-mentioned and other advantages and objects of this invention, and the manner of attaining them, will become more apparent, and the invention itself will be better understood, by reference to the following description of embodiments of the invention taken in conjunction with the accompanying drawings, wherein.

Corresponding reference characters indicate corresponding parts throughout the several views. Although the drawings represent an embodiment of the present invention, the drawings are not necessarily to scale, and certain features may be exaggerated or omitted in some of the drawings in order to better illustrate and explain the present invention.

DETAILED DESCRIPTION

Figure 1:
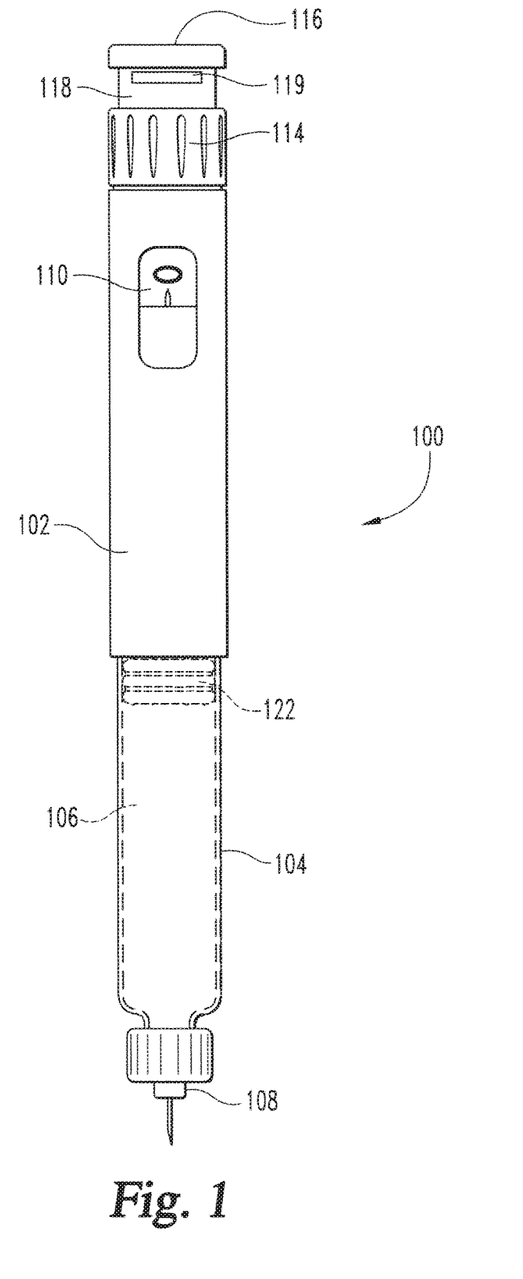
FIG. 1 is a front view of a medication delivery device equipped with a zero position sensing system, which device is shown arranged in a zero position.

In FIG. 1, there is shown a medication delivery device in which a sensing system for determining a zero position of the device is advantageous employed. The device is a pen-shaped medication injection device, generally designated 100, which is manually handled by a user to selectively set a dose and then to inject that set dose. Injection devices of this type are well known, and the description of device 100 is merely illustrative as the sensing system can be adapted for use in variously constructed pen-shaped medication injection devices, as well differently shaped injection devices and other medication delivery devices in general.

Medication injection device 100 includes a housing that supports the internal components of the device. The housing is shown as having a rear or proximal housing portion 102 that holds therein a mechanical drive mechanism of the device. A forward or distal housing portion 104 holds a cartridge 106 filled with medication. By operating device 100, a user can cause the medication in cartridge 106 to be delivered in one or more doses through a needle assembly 108 mounted to the forward end of the housing portion 104.

Medication injection device 100 is shown in FIG. 1 in its "zero position". This zero position refers to a mechanical arrangement of the component parts of device 100 at which the device when new may be provided initially to a user, or at which the device is arranged, for example, just after a prior injecting use of the device has been properly completed. A dial numbering "0" visible in the dose display 110 generally indicates the device is arranged at the zero position.

Figure 2:
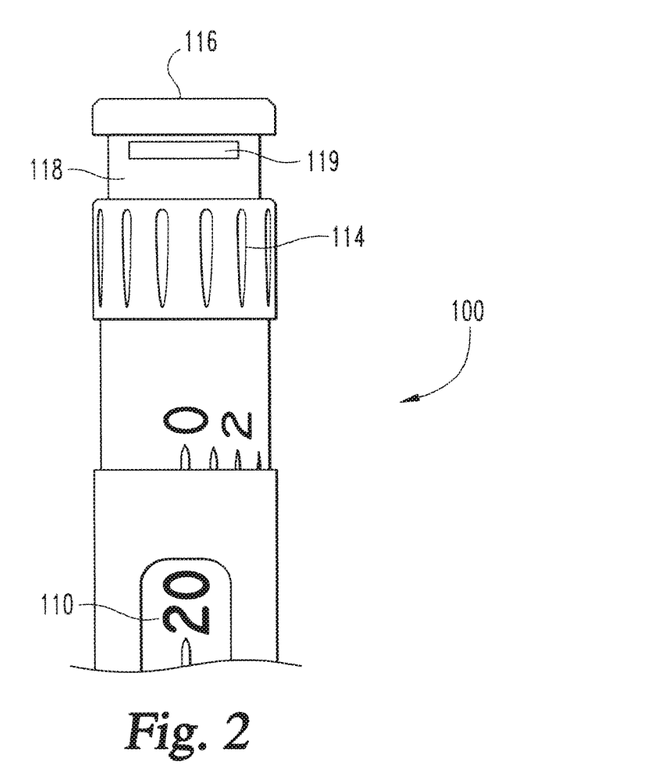
FIG. 2 is a partial front view of the device of FIG. 1 after being set to deliver a dose.

As with many known injection devices, device 100 when arranged as shown in FIG. 1 may then be set to deliver a dose by a user gripping and turning a dose setting collar or grip 114 relative to housing portion 102. Due to the configuration of device 100, this turning results in collar 114 screwing outward from housing portion 102, and the user may stop the collar turning when a desired dose for delivery is set. Such desired set dose could be determined by viewing the number visible in dose display 110. In FIG. 2, device 100 is shown after having been set by the user to deliver twenty units of medication, as recognizable by the presence of "20" within dose display 110. Alternatively, or additionally, a set dose may be displayed in a not shown electronic display of device 100.

To deliver that set dose, while holding the device housing, a user applies a plunging force on the top surface 116 of a button 118 carried by the collar 114. The top surface 116 is part of a button cap that is rotatable relative to the rest of button 118, such as due to an interposed thrust bearing. This plunging force first moves the button 118 axially further into collar 114 to a shifted downward position, after which the continuing plunging force causes collar 114 to screw back into housing portion 102 to its axial position shown in FIG. 1. As the collar 114 so screws back, the button 118 remains in its shifted downward position within the collar and screws in with the collar 114 relative to housing portion 102, while the drive mechanism of device 100 extends its output member from housing portion 102 to advance a cartridge plunger 122 forward within cartridge 106 to expel medication through needle assembly 108.

Figure 3:
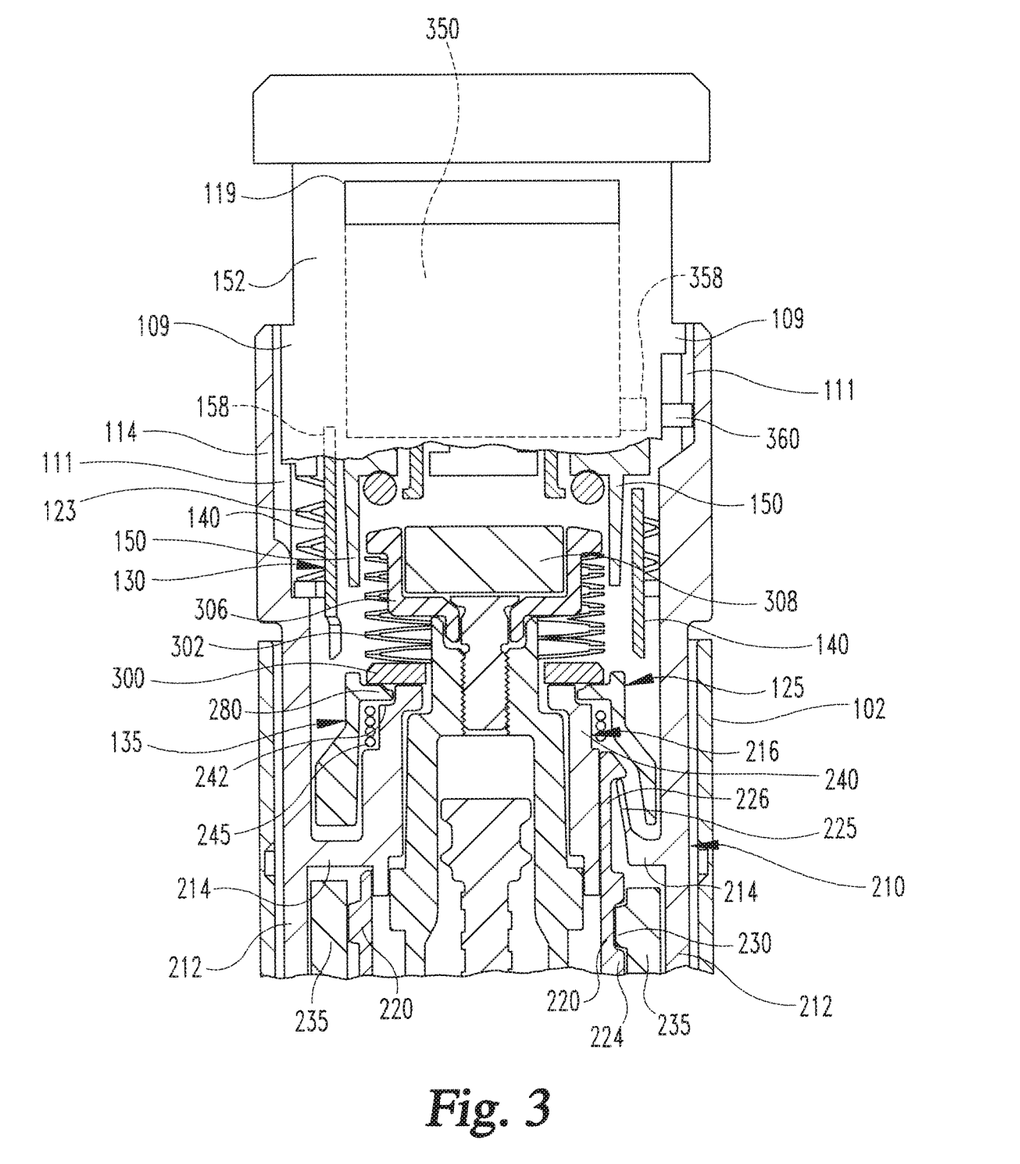
FIG. 3 is partial front view of the device of FIG. 1 in which select parts are shown in longitudinal cross-section.
Figure 4A:
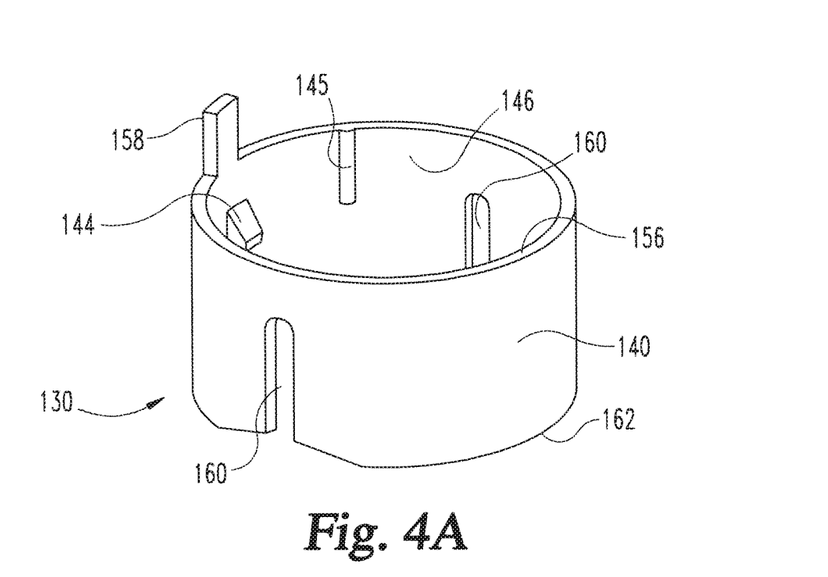
FIGS. 4A and 4B are different perspective views of one actuator member of the sensing system of FIG. 1.
Figure 4B:
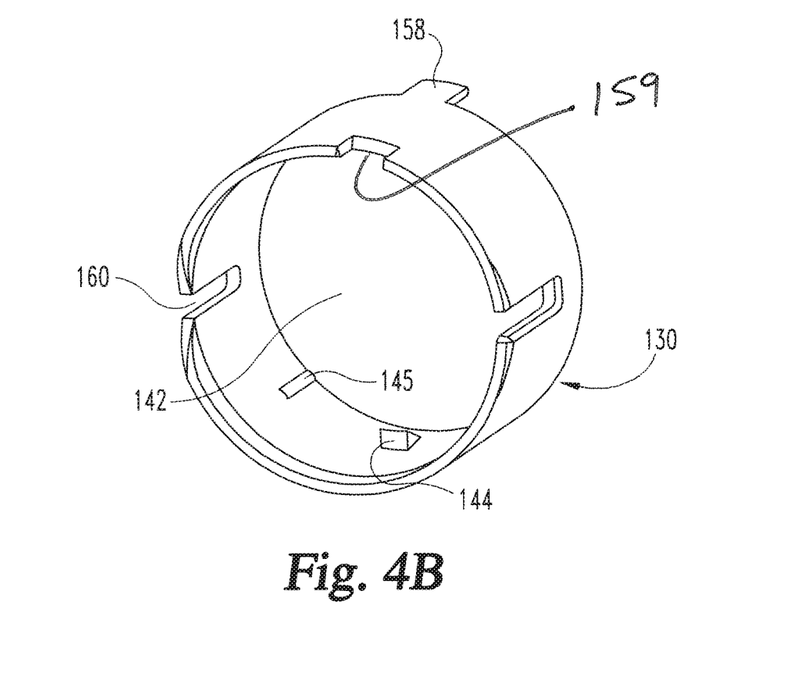
Figure 5A:
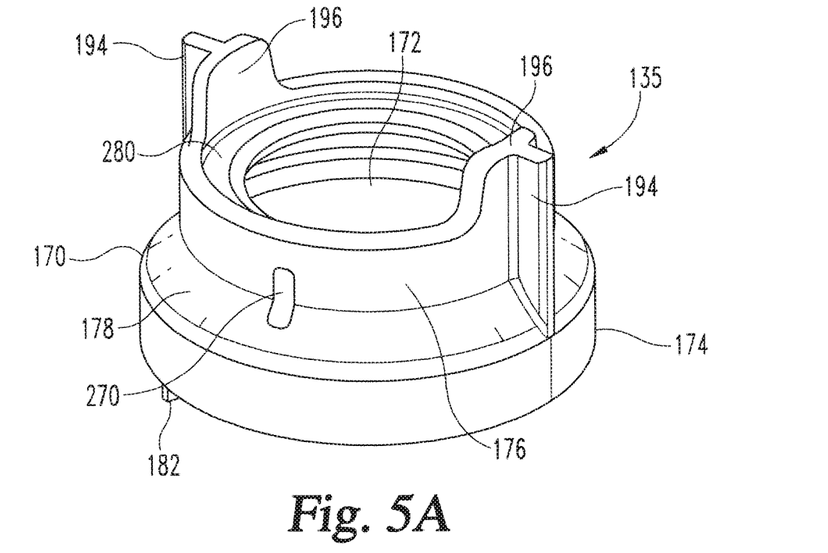
FIGS. 5A and 5B are different perspective views of another actuator member of the sensing system of FIG. 1.
Figure 5B:
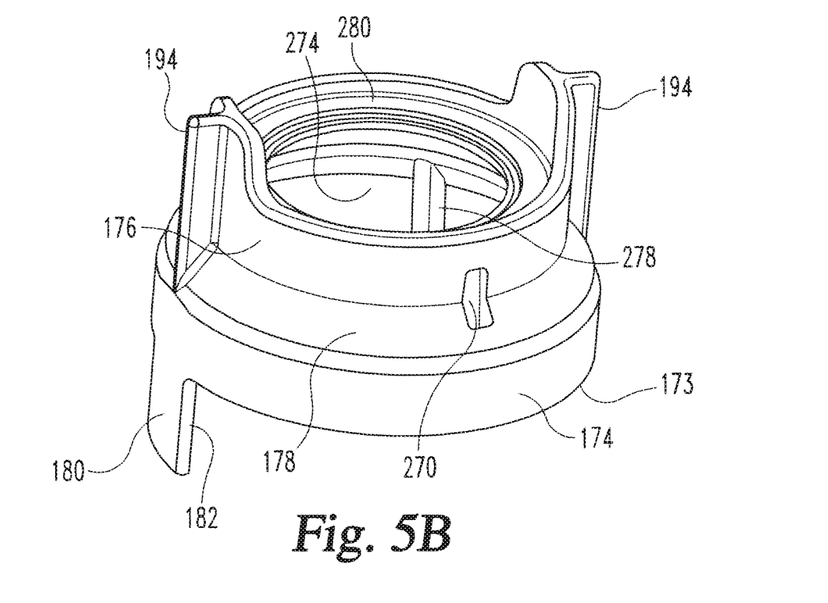
Figure 6:
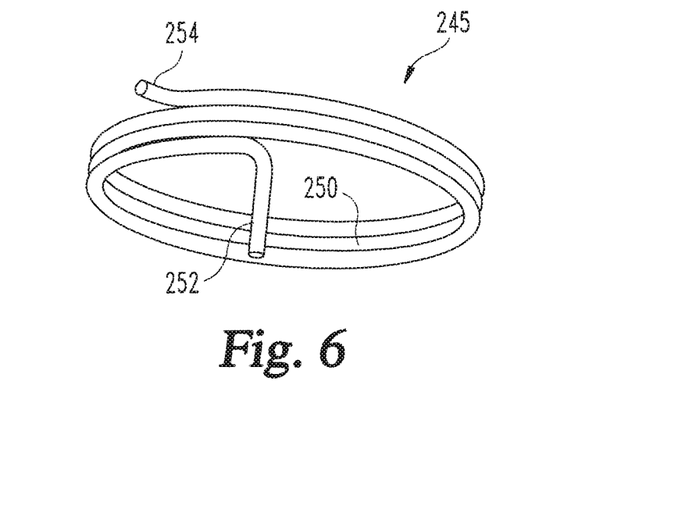
FIG. 6 is a perspective view of a biasing member of the sensing system of FIG. 1.
Figure 7:
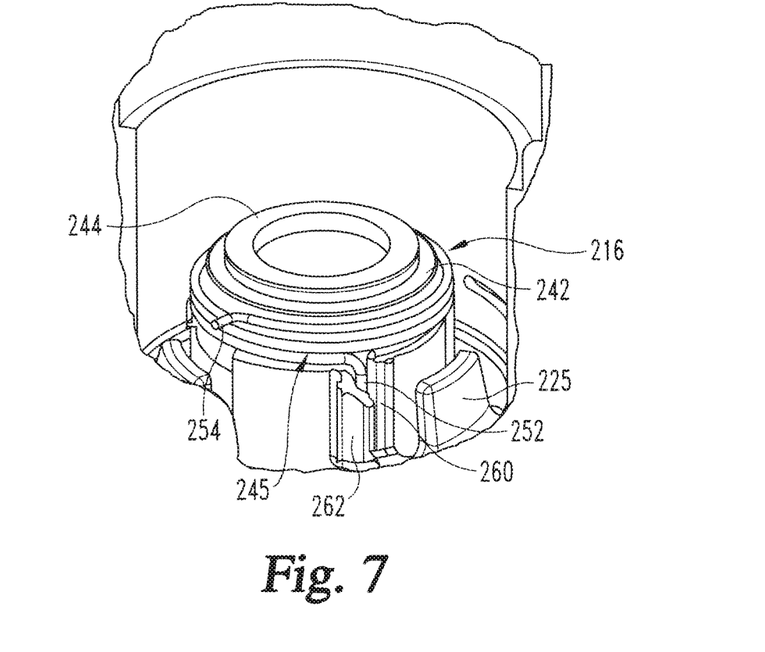
FIG. 7 is a partial perspective view of the device of FIG. 1 with portions removed, showing the biasing member of FIG. 6 mounted to a screw element.

The button 118 of device 100 includes an electronics module, shown abstractly at 350 in FIG. 3, which can provide one or more of a variety of functions as is known in the art. Electronics module 350 may interface with device components, such as using magnetic or optical or audible sensing or the like, to determine a dose being injected. Electronics module 350 may control a display, such as a light display visible on the side of the button at 119 that indicates device condition, or a not shown electronic display, such as on the end of the device and visible through surface 116, which shows injection data, such as time or amount of a dose. Electronics module 350 may control wireless communications with a smart system such as a phone or computer or cloud database, which uses and/or shows the device injection data.

After the injection is completed, when a user removes the plunging force from top surface 116, the button 118, due to a force provided by a spring 123 compressed during plunging, returns upward within the collar 114 to the position shown in FIG. 1, and device 100 is again arranged as shown in FIG. 1.

The zero position sensing system described herein can be adapted for use with variously configured devices having different components that experience a screwing motion relative to their housings during medication delivery. The specific manner in which the internal drive mechanism of device 100 converts the motion of button 118/collar 114 into advancement of the cartridge plunger-engaging output member does not form a part of the invention and is therefore described only generally herein, and such can be provided by one of a variety of known drive mechanisms.

With reference now to FIGS. 3-8, the sensing system, generally designated 125, and other select portions of device 100 are shown in additional detail. Sensing system 125 includes a first actuator member 130 and a second actuator member 135. The use of two cooperating actuator members provides one manner of accounting for the axial movement but not rotational movement between the electronics module 350 and a screw element of device 100 during injection. Alternate sensing systems could be adapted to use a single actuator member, or additional interacting actuator members if a more complicated connection chain were required.

Actuator member 130 is a rigid bushing formed of molded plastic with a ring-shaped body 140 that defines a central opening 142. Body 140 need not be ring-shaped or circular, but such provides desirable rigidity and allows for a balanced interaction with actuator member 135. A pair of diametrically spaced detents 144 on the inner surface 146 of body 140 allow for a snap fit to a depending flange 150 of the button housing 152 which fits within opening 142. Flange 150 is provided with openings or grooves (not shown) in which detents 144 can slide to allow actuator member 130 to rotate but not move axially relative to flange 150 and housing 152. Three ribs 145 on inner surface 146 provide contact points, arranged on the same circumference, for contacting depending flange 150 of the button housing 152 in order to allow easier dimensional control and tuning in manufacturing.

Actuator member 130 includes an axially upstanding, rectangular flange 158 that projects above the upper rim 156 of body 140. Flange 158 projects within button housing 152 through an opening therein. Notch 159 on the bottom edge of body 140 provides space for the end of spring 245 when the system is compressed.

Actuator body 140 also includes key features for cooperating with complementary features of the actuator member 135. The features are shown as keyways formed by two axially extending slots 160 that extend up from bottom edge 162 of body 140. Slots 160 are diametrically disposed on body 140.

Actuator member 135 is a rigid bushing formed of molded plastic with a ring-shaped body 170 that defines an open-ended interior volume 172. Like body 140, body 170 need not be ring-shaped or circular. Along its axial height, the exterior radial periphery of body 170 includes a larger diameter base region 174, a smaller diameter upper region 176, and a tapering region 178 transitioning therebetween. Body upper region 176 is sized to fit within central opening 142 of actuator member 130.

Actuator member 135 includes an axially depending, rectangular flange 180 that projects below the lower edge 173 of body base region 174. Flange 180 extends through an opening 190 (See FIG. 8) in annular spanning section 214. An axially oriented edge 182 of flange 180 serves as a contact or push surface of actuator member 135.

A pair of key features in the form of radially projecting and axially oriented ribs 194 are disposed on the outer radial periphery of body upper region 176 and tapering region 178 as well as on support extensions 196 formed on upper region 176. Ribs 194 are shaped and arranged to fit within slots 160 so that actuator members 130 and 135 are axially movable relative to one another but rotatably fixed together when assembled in device 100.

Actuator member 135 is mounted on a part of device 100 that moves with a screwing motion in housing portion 102 during injection, and which part is therefore termed a screw element. The screw element, generally designated 210, is shown in FIG. 3 as an outer piece and an inner dialing screw piece that are rigidly interconnected together during device assembly. Screw element 210 extends in an axial direction within device 100. The outer piece provides the collar 114, a cylindrical tube portion 212, an annular spanning section 214, and an upstanding hub portion, generally designated 216, all integrally formed together. To facilitate manufacture, the collar 114 as well as other outer piece parts may be separately formed and then attached to tube portion 212. Dose-indicating numbers provided in a helical pattern on the outer radial periphery of tube portion 212 are visible within dose display 110 in a conventional fashion.

The inner dialing screw piece of screw element 210 includes a tube 220 with external threading 224, which tube 220 includes extensions 226 at its proximal end which closely fit through complementary openings in spanning section 214 and snap fit in latching engagement with angled flanges 225 of hub portion 216 projecting upward from spanning section 214. Threading 224 threadedly engages complementary threading 230 provided on the radially interior surface of a tubular support 235.

Tubular support 235 is held both rotatably fixed and axially fixed within the interior hollow of housing portion 102, such as by being directly fastened to the interior wall of housing portion 102. The engagement of threading 224 with threading 230 results in screw element 210 moving in a screwing motion relative to housing portion 102 as it turns in one direction, generally, during dose setting and the opposite direction during injecting.

Hub portion 216 includes a reduced diameter portion 240 around which fit the coils 250 of a torsion spring 245. An axially extending finger 252 of spring 245 depends from the bottom coil of coils 250 and fits into a recess of the hub portion 216 defined by ribs 260 and 262. A radially projecting finger 254 extends from the upper coil of coils 250 and fits into a slot 270 formed through upper region 176 of actuator member 135. Torsion spring 245, when fingers 252 and 254 are captured within the hub portion recess and slot 270 respectively, serves as a biasing member of the sensing system which resists rotational movement of actuator member 135 around hub portion 216 from a first angular position to a second angular position. In alternate embodiments, this biasing can be achieved with different biasing members, such as a compression spring configured to provide a resistance to actuator member rotation.

The interior surface 274 of actuator member body 170 is designed to accommodate the outer periphery of hub portion 216 including its flanges 225 and ribs 260, 262. Three ribs 278 projecting inward from surface 274 serve to provide bearing surfaces at which actuator member 135 is supportably contacted by the hub portion 216 as it rotatably pivots about that hub portion. An annular flange 280 projecting inward from body upper region 176 is supported by a ledge 242 formed by a circumferential notch in the upper face 244 of hub portion 216. Actuator member 135 is able to rotationally pivot on hub portion 216 between different angular positions when flange 280 slides on ledge 242.

Actuator member 135 is in use effectively axially fixed to the screw element 210 to move axially identically thereto due to flange 280 being captured between ledge 242 and thrust washer 300. Washer 300 is pressed against upper face 244 by a compression spring 302 that at its opposite end acts against a magnet support 306 that holds a magnet 308 used by electronics module 350 to measure relative movement of device parts during an injection operation to determine an injection amount.

Electronics module 350 is protectively housed within housing 152 of button 118. Electronics module 350 and its housing 152 are rotatably fixed with screw element 210 due to button 118 and collar 114 being keyed together via splines 109 and grooves 111 to allow axial movement but not rotational movement therebetween. Electronics module 350 includes a sensor indicated at 355 (See FIG. 8) that cooperates with the actuator member 130 to sense its rotational position. One suitable sensor 355 is an electrical switch that changes state, such as closed to open, or open to closed, when actuator member flange 158 rotationally pivots with actuator member 130 relative to sensor 355 as described further below. In alternate embodiments, and with any suitable adaptations in the actuator member, a different type of sensor, for example a magnetic or optical sensor, can be used as sensor 355.

Electronics module 350, in addition to sensor 355, may include a power obtaining feature such as a rechargeable battery or an energy harvesting system. Electronics module 350 is also shown in FIG. 3 as including a cammable switch 358 that is operated by a switch push 360 that is driven radially inward by engagement with the interior of collar 114 when button 118 is pushed into the collar 114 during injection, where the operation of the cammable switch 358 indicates to the electronics module 350 that the button is being pushed down during the start of an injection.

Figure 8:
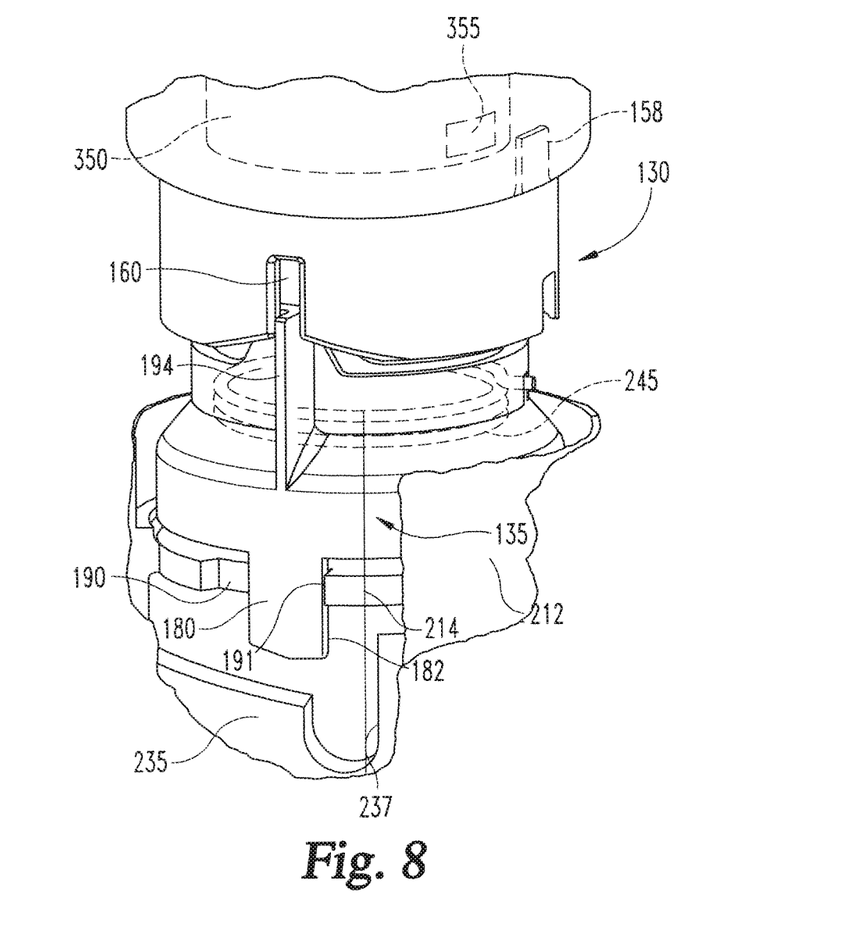
FIG. 8 is a partial perspective view of the device of FIG. 1 with portions removed, further showing the sensing system after the device has been operated to set a dose.

When sensing system 125 is installed within device 100 during manufacturing assembly, actuator member 135 is mounted to screw element 210 so as to place torsion spring 245 in a preloaded state. This preloading torques actuator member 135 such that edge 182 of flange 180 is pressed or held against an angular end of the arcuate slot 190 in annular spanning section 214, and in particular against the angular end formed by the surface 191 that defines such arcuate slot 190. The portion of edge 182 that depends below annular spanning section 214 is adapted to engage a stop surface adapted to push actuator member 130 to rotate about the screw element 210. The stop surface in device 100 is shown in FIG. 8 as a vertically oriented surface 237 provided on tubular support 235. Stop surface 237 is arranged within the housing 102 to be abutted initially by push surface 182 when screw element 210 has nearly screwed to the zero position from a dosing position. The stop surface could be otherwise provided within the housing in alternate embodiments, such as being formed directly on an inside surface of housing portion 102.

After such initial abutment, as screw element 210 continues to screw down until it reaches the zero position, the abutment forces the actuator member 130 to move relatively around the screw element hub portion 216 from a first angular position, at which electrical switch 355 is, for example, open, to a second angular position at which electrical switch 355 is, for example, closed, against a biasing or resistance to such movement by torsion spring 245. The switching of switch 355 signals that the zero position of the device has been reached. The rotation required of actuator member 135 and therefore actuator member 130 relative to screw element 210 and electronics module 350 to activate the switch 355 is a function of the operational spacing of sensor 355 and flange 158. Such spacing is preferably such that during injection the push surface 182 first comes into contact with stop surface 237 when the mechanical components of device 100 still have to move an amount approximately equivalent to the dispensing of a single unit before reaching a zero, or end of dose, position.

Figure 9:
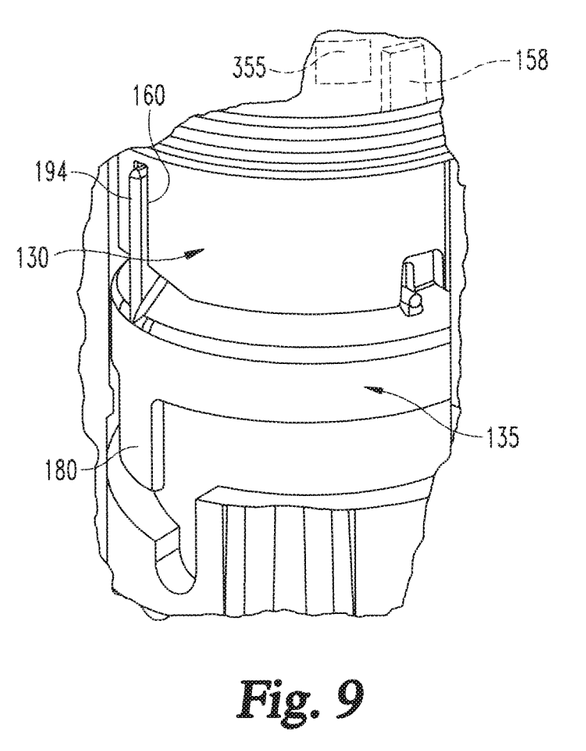
FIGS. 9-11 are partial perspective views of the device of FIG. 1 with portions removed, further showing the sensing system at various stages of the device being operated to deliver a previously set dose.

The structure of sensing system 125 will be further understood in view of the following description of how it can function during a dose injection. Specifically, after a desired dose is set for device 100, and when a sufficient plunging force is applied to top surface 116 as described above, the movement of button 118 into collar 114 is accounted for in the sensing system 125 by actuator member 130 moving axially relative to actuator member 135 such that slots 160 further slide down over ribs 194. FIG. 8 shows the axial spatial relationship of actuator members 130 and 135 during dosing, and FIG. 9 shows the axial spatial relationship of actuator members 130 and 135 after the button moves into the collar during injecting.

As the plunging force on top surface 116 continues and screw element 210, as well as the button 118 held within collar 114, screw into housing 102, the sensing system 125 will recognize that the zero position has not been reached, and furthermore will move with screw element 210, unless and until the device is sufficiently near its zero position so as to begin the rotational shifting of the sensing system about the screw element. In particular, because the preloading of torsion spring 245 maintains the angular position of actuator member 135 on screw element 210 such that flange 180 presses against the end of slot 190, and due to the keyed relationship of actuator members 135 and 130 and the fact that button 118 moves with screw element 210, actuator members 135 and 130 move with screw element 210 and electronics module 350. During this movement, flange 158 remains clear of switch 355, and consequently the electronics module 350 recognizes that actuator member 130 is not in its position associated with the zero position of device 100. Sensing system 125 during this time will be configured as is shown in FIG. 9.

Figure 10:
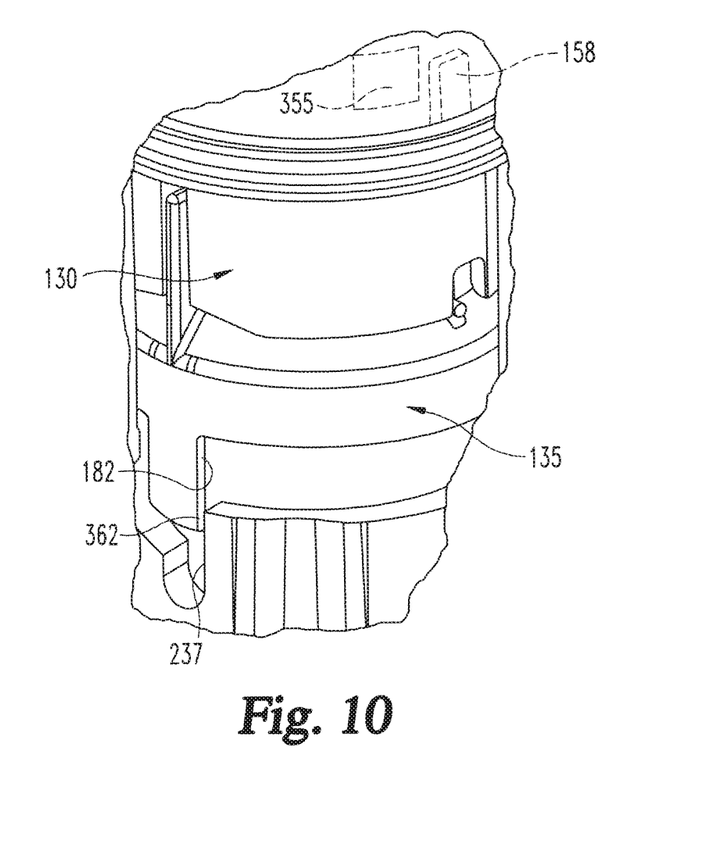

As the plunging force on top surface 116 continues to force the screw element 210 to screw inward, screw element travel results in sensing system 125 approaching stop surface 237. FIG. 10 illustrates device 100 at this point of injection and at which only a small angular gap 362 remains between flange edge 182 and stop surface 237, and for device 100 this arrangement occurs when the number "1" is indicated in dose display 110.

Figure 11:
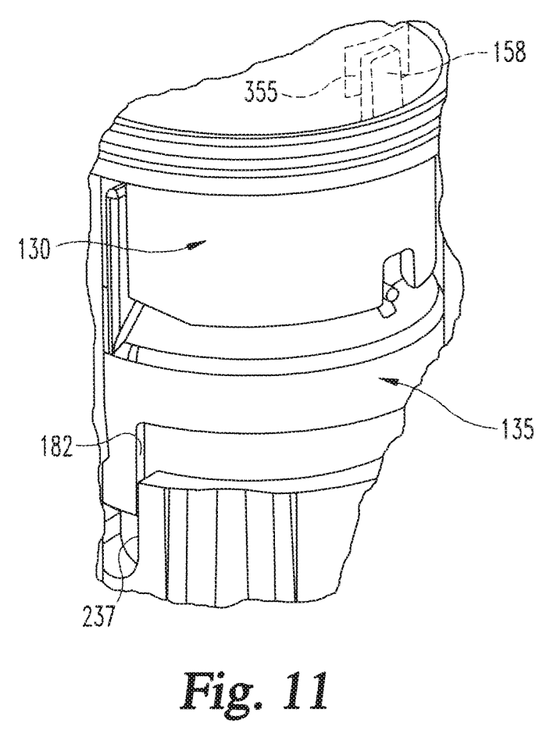

As the plunging force on top surface 116 continues to force the screw element 210 to screw inward, flange edge 182 abuts stop surface 237 so that further screwing motion relative to housing portion 102 of actuator member 135, as well as actuator member 130, is physically prevented. As the screw element 210 continues to be screwed into housing portion 102 with sufficient force to overcome resistance provided by torsion spring 245, actuator members 135 and 130 experience rotation relative to hub portion 216 and the rest of screw element 210, as well as button 106. During this relative rotation, and as the device 100 finally reaches its zero position, sensor 355 is brought into operational contact with flange 158, whereby sensor 355 is activated and electronics module 350 recognizes that the zero position of device 100 has been reached. FIG. 11 illustrates device 100 at this point of device operation. Electronics module 350 can then use and possibly communicate that recognition to a user in any suitable fashion. The actual plunging or screw travel of screw element 210 can be physically stopped within housing 102 in any known fashion, such as by annular spanning section 214 bottoming out on the top edge of tubular support 235, which stopping will be, within tolerances, as soon as possible after the zero position recognition via sensor 355 has occurred.

While this invention has been shown and described as having preferred designs, the present invention may be modified within the spirit and scope of this disclosure. For example, the sensing system can be mounted on different screwing elements than the one shown in the illustrated embodiment. This application is therefore intended to cover any variations, uses or adaptations of the invention using its general principles. Further, this application is intended to cover such departures from the present disclosure as come within known or customary practice in the art to which this invention pertains.

I claim:

1. A sensing system for determining a zero position of a medication delivery device, the medication delivery device including a housing, a screw element, and an electronics module, the screw element screwable within the housing from a dosing position to a zero position during dose delivery, the sensing system comprising:
   at least one actuator member mounted to be movable relative to the screw element from a first angular position to a second angular position, said at least one actuator member including a push surface;
   a biasing member comprising a torsion spring arranged to resist motion of said at least one actuator member from said first angular position to said second angular position;
   a stop surface structured and arranged within the housing to be in an abutment relationship with said push surface as the screw element screws to the zero position from the dosing position, wherein in response to the abutment relationship said at least one actuator member is forced to move from said first angular position to said second angular position against resistance provided by said biasing member; and
   a sensor within the electronics module adapted to recognize said at least one actuator member at said second angular position thereby to sense that the zero position has been reached.

2. The sensing system of claim 1 wherein said screw element extends in an axial direction, said at least one actuator member comprising first and second actuator members with cooperating keying elements that prevent relative rotational motion and permit relative axial motion between said first and second actuator members.

3. The sensing system of claim 2 wherein said first actuator member is axially movable relative to said sensor and said second actuator member is axially fixed relative to said sensor, said first actuator member including said push surface.

4. The sensing system of claim 1 wherein the torsion spring has first and second ends, said first end engaged with the screw element and said second end engaged with said at least one actuator member.

5. The sensing system of claim 4 wherein said torsion spring is preloaded when said at least one actuator member is at the first angular position, said at least one actuator and the screw element including cooperating stop elements to prevent said at least one actuator member from moving past the first angular position under the preloaded biasing of said torsion spring.

6. The sensing system of claim 5 wherein said stop element of said at least one actuator comprises a surface of a flange that extends from a body of said at least one actuator.

7. The sensing system of claim 6 wherein said push surface is disposed on said flange.

8. The sensing system of claim 6 wherein said stop element of the screw element comprises an opening-defining surface.

9. The sensing system of claim 8 wherein said opening-defining surface defines an arcuate slot in which said flange travels when said at least one actuator member moves from said first angular position to said second angular position.

10. The sensing system of claim 1 wherein said at least one actuator member comprises a ring-shaped body that encircles a portion of the screw element.

11. The sensing system of claim 10 wherein said at least one actuator member comprises first and second actuator members, each of said first and second actuator members comprising a ring-shaped body, and wherein a portion of said ring-shaped body of said second actuator fits within said ring-shaped body of said first actuator.

12. The sensing system of claim 1 wherein said sensor comprises an electrical switch.

13. The sensing system of claim 12 wherein said at least one actuator includes a projection that operates said electrical switch when said at least one actuator is disposed at said second angular position.

14. A medication delivery device with a sensing system for determining a zero position of the medication delivery device, comprising:
   a housing,
   a screw element screwable within and relative to the housing from a dosing position to a zero position during dose delivery,
   an electronics module,
   at least one actuator member mounted to be movable around the screw element from a first angular position to a second angular position, said at least one actuator member including a push surface;
   a biasing member comprising a torsion spring arranged to resist motion of said at least one actuator member from said first angular position to said second angular position;
   a stop surface structured and arranged within the housing to be in an abutment relationship with said push surface as the screw element, with said at least one actuator member, screws relative to the housing towards the zero position from the dosing position during dose delivery, the abutment relationship configured to inhibit further screwing of said at least one actuator relative to the housing and to force said at least one actuator member to move from said first angular position to said second angular position against resistance provided by said biasing member, as the screw element continues to be screwed relative to the housing to the zero position; and
   a sensor within the electronics module adapted to recognize said at least one actuator member at said second angular position.

15. The device of claim 14, wherein said torsion spring is preloaded when said at least one actuator member is at the first angular position.

16. The device of claim 15, wherein said at least one actuator member and the screw element include cooperating stop elements to prevent said at least one actuator member from moving past the first angular position under the preloaded biasing of said torsion spring.

17. The device of claim 14, wherein said screw element extends in an axial direction, said at least one actuator member comprising first and second actuator members with cooperating keying elements that prevent relative rotational motion and permit relative axial motion between said first and second actuator members.

18. The device of claim 14 wherein said at least one actuator member comprises a ring-shaped body that encircles a portion of the screw element.

19. A sensing system for determining a zero position of a medication delivery device, the medication delivery device including a housing, a screw element, and an electronics module, the screw element screwable within the housing from a dosing position to a zero position during dose delivery, the sensing system comprising:
   at least one actuator member mounted to be movable relative to the screw element from a first angular position to a second angular position, said at least one actuator member including a push surface;
   a biasing member comprising a torsion spring arranged to resist motion of said at least one actuator member from said first angular position to said second angular position, wherein said torsion spring is preloaded when said at least one actuator member is at the first angular position;
   a stop surface structured and arranged within the housing to be in a circumferential abutment relationship with said push surface as the screw element screws to the zero position from the dosing position, the circumferential abutment relationship configured to force said at least one actuator member to rotate from said first angular position to said second angular position against resistance provided by said torsion spring; and
   a sensor within the electronics module adapted to recognize said at least one actuator member at said second angular position.

20. The device of claim 19, wherein at least one of said at least one actuator member and the screw element include cooperating stop elements to prevent said at least one actuator member from moving past the first angular position under the preloaded biasing of said torsion spring and wherein said sensor comprises an electrical switch.

* * * * *

UNITED STATES PATENT AND TRADEMARK OFFICE
CERTIFICATE OF CORRECTION

PATENT NO. : 11,357,923 B2
APPLICATION NO. : 15/760835
DATED : June 14, 2022
INVENTOR(S) : Gabriele Ganzitti It is certified that error appears in the above-identified patent and that said Letters Patent is hereby corrected as shown below:

In the Claims

Column 10, Line 52, "device" should read --sensing system--

Signed and Sealed this
Fourteenth Day of March, 2023

Katherine Kelly Vidal
*Director of the United States Patent and Trademark Office*